United States Patent
Moore

(10) Patent No.: US 6,920,662 B2
(45) Date of Patent: *Jul. 26, 2005

(54) CLEANING BRUSH FOR MEDICAL DEVICES

(75) Inventor: P. Timothy Moore, Englewood, CO (US)

(73) Assignee: Neosci Medical, Inc., Draper, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/778,746

(22) Filed: Feb. 13, 2004

(65) Prior Publication Data

US 2004/0158945 A1 Aug. 19, 2004

Related U.S. Application Data

(63) Continuation of application No. 09/826,258, filed on Apr. 3, 2001, now Pat. No. 6,725,492, which is a continuation-in-part of application No. 09/441,867, filed on Nov. 17, 1999, now abandoned.
(60) Provisional application No. 60/109,769, filed on Nov. 25, 1998.

(51) Int. Cl.⁷ .................................................. B08B 9/00
(52) U.S. Cl. ................ 15/104.2; 15/104.16; 401/282; 401/284; 604/267
(58) Field of Search ..................... 15/104.16, 104.2, 15/164, 206; 401/268, 282–291; 604/264, 266, 267

(56) References Cited

U.S. PATENT DOCUMENTS

| | | | | |
|---|---|---|---|---|
| 1,173,721 A | * | 2/1916 | Hurvitz | 401/278 |
| 1,332,266 A | * | 3/1920 | McDonald | 401/10 |
| 1,778,552 A | * | 10/1930 | Floyd | 401/290 |
| 1,825,929 A | * | 10/1931 | Voigt | 15/206 |
| 2,232,358 A | * | 2/1941 | Baerer | 401/9 |
| 4,235,244 A | * | 11/1980 | Abele et al. | 600/562 |
| 4,819,291 A | * | 4/1989 | Gunjian | 15/104.2 |
| 4,858,360 A | * | 8/1989 | Hardin | 42/95 |
| 4,889,106 A | * | 12/1989 | Watanabe | 600/101 |
| 5,168,593 A | * | 12/1992 | Poje et al. | 15/104.2 |
| 5,253,386 A | * | 10/1993 | LaLonde | 15/206 |
| 5,297,310 A | * | 3/1994 | Cox et al. | 15/106 |
| 5,405,755 A | * | 4/1995 | Markus et al. | 435/34 |
| 5,407,807 A | * | 4/1995 | Markus | 435/34 |
| 5,474,075 A | * | 12/1995 | Goldberg et al. | 600/463 |
| 5,491,863 A | * | 2/1996 | Dunn | 15/106 |
| 5,535,756 A | * | 7/1996 | Parasher | 600/569 |
| 5,560,069 A | * | 10/1996 | Berger et al. | 15/160 |
| 5,615,439 A | * | 4/1997 | Bourrelly | 15/104.2 |
| 5,871,589 A | * | 2/1999 | Hedge | 134/8 |
| 6,045,623 A | * | 4/2000 | Cannon | 134/8 |
| 6,047,431 A | * | 4/2000 | Canonica | 15/104.095 |
| 6,122,792 A | * | 9/2000 | Roy | 15/104.2 |

* cited by examiner

*Primary Examiner*—Mark Spisich
(74) *Attorney, Agent, or Firm*—Workman-Nydegger

(57) ABSTRACT

A brush for in situ cleaning of one or more passageways defined by a medical device. The brush includes a NiTiNOL shaft attached to a fill section by way of a proximal connector sleeve that is resistance welded to the fill section and the shaft. The fill section is preferably composed of braided wire and includes bristles, or fill, interweaved with the braided wire. The fill section in turn, is attached to an atraumatic tip by way of a distal connector sleeve which is resistance welded to the fill section and the atraumatic tip. The atraumatic tip includes a NiTiNOL core wire about which is disposed a gold-plated tungsten coil readily visible under a fluoroscope. The coil is bonded to the core wire. A bulb disposed on the coil helps effectuate cleaning of the passageway while also protecting the patient and the medical device from cleaning-related trauma.

28 Claims, 7 Drawing Sheets

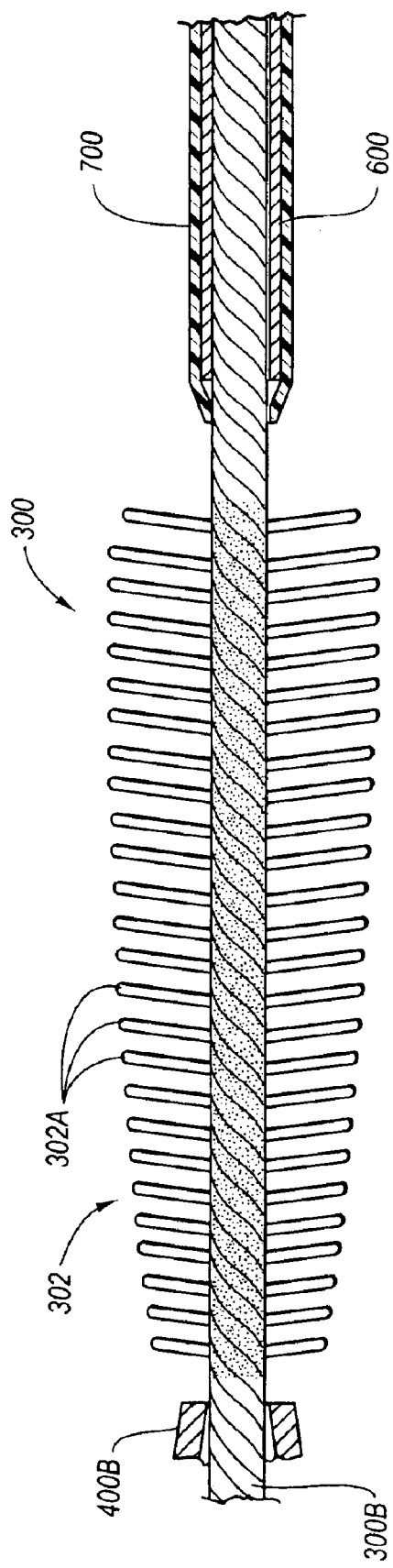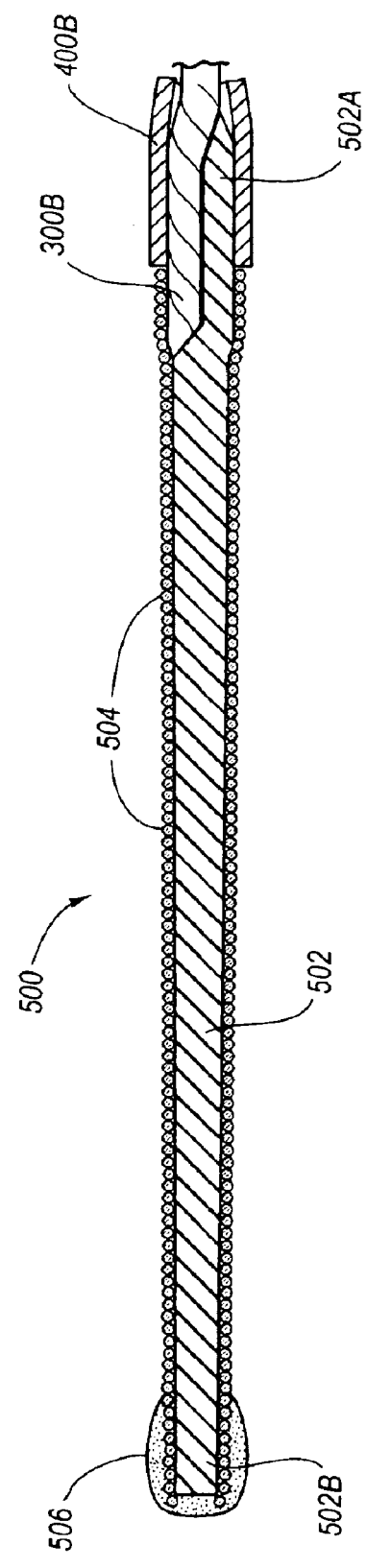
FIG. 7
FIG. 8

CLEANING BRUSH FOR MEDICAL DEVICES

RELATED APPLICATIONS

This application is a continuation of Ser. No. 09/826,258 filed Apr. 3, 2001 now U.S. Pat. No. 6,725,492, issued Apr. 27, 2004; which is a continuation-in-part of U.S. patent application Ser. No. 09/441,867, filed Nov. 17, 1999, now abandoned; which claims the benefit of U.S. Provisional Patent Application Ser. No. 60/109,769, filed on Nov. 25, 1998; all of which are incorporated herein in their entirety by this reference.

BACKGROUND OF THE INVENTION

1. The Field of the Invention

The present invention relates to apparatuses used to clean medical devices. In particular, the present invention relates to a brush for safely and effectively cleaning the interior passageway of medical devices such as hemodialysis tubes, catheters, feeding tubes, and venous lines, without necessitating removal of the medical device from the patient.

2. The Relevant Technology

Various types of tubular medical devices have been employed in the medical field to perform a broad range of important functions. For example, catheters are commonly employed to carry various bodily fluids, including but not limited to, abscess fluids, urinary fluids, or biliary fluids. Other such medical devices include feeding tubes, used to provide nutrition to a patient, hemodialysis tubes, and venous lines.

Many of these medical devices are used in long-term treatments. It is important that the interior passageway in these medical devices remain unobstructed. Accordingly, various cleaning devices have been developed which are intended to remove matter such as particles, residues, and the like, which may collect in the interior passageway, or other portions, of the medical device. Some types of medical devices include a retention string which resides inside the device and is used to control the device during placement. One problem associated with such retention string arrangements is that residue or particles may build up on the retention string itself. Such buildup may lead to uneven, reduced, or obstructed flow in the tubular medical device. Obstructed or limited flow may extend the recovery time of a patient, resulting in the potential for further complications or infections. For example, an infection may cause complications in the patient's treatment leading to sickness or even death. These problems are exacerbated in those cases where the medical device must be kept in place for a relatively long period of time.

Presently, many of these types of medical devices are periodically exchanged for a new instrument. Typically, the life of the medical device is limited by buildup in the interior passageway. As a result, after a certain amount of time, the medical device is removed and discarded and a new device is then inserted. Inserting a new medical device however, often implicates additional risks of inducing infection. In addition, the replacement of the medical device increases the overall cost to the patient. Thus, each replacement of the medical device implicates a variety of undesirable effects, including increased pain to the patient, increased expenses, and increased potential for inducing an infection which could jeopardize the health of the patient.

As suggested earlier, various specialized instruments have been developed for use in conjunction with tubular type medical devices. However, as discussed below, none of these devices are designed to permit cleaning of the tubular medical device while the medical device is attached to and fluidly connected to the patient.

One example of such a device is a cytology brush such as is used to collect cells for analysis. The cytology brush is basically an elongated brush which includes soft bristles. The brush is passed through an endoscope or coaxial catheter and pushed so that the bristles brush over the end wall of the duct to displace cells from the duct wall. Some of the cells are captured in the bristles. By design, cytology brushes are intended to collect cells and are not structurally equipped to apply the scrubbing forces necessary for removal of particles, residue, or the like from the interior passageway of a medical device.

A brush apparatus is also available that is used to detect whether a catheter is a cause of an infection in a patient, without necessitating removal of the catheter from the patient to perform the detection process. Typically, the apparatus includes a wire handle, brush, and a protective, microbially impervious bag disposed over the handle and brush. The device is used by advancing the brush in the catheter and simultaneously removing it from the protective bag. After the sample has been obtained, the brush is retracted. Once the brush is fully retracted, the wire to which the brush is attached is clipped and the brush is placed into the bag, or a vial.

Yet another type of brush that is available is a motorized brush that is inserted through a catheter, over a guidewire, into a blood vessel. In use, the brush extends beyond the catheter and is used to break up blood clots in the blood vessel.

Finally, a brush-tipped catheter is available which includes a biopsy brush that comprises a plurality of bristles that extend from the distal end of a catheter sheath itself. Such biopsy brushes are typically employed in the context of peripheral transbronchial biopsies to obtain samples.

In view of the foregoing problems and shortcomings, it would be an advancement in the art to provide a brush that facilitates, among other things, safe and effective in situ cleaning of tubular medical devices such as hemodialysis tubes, catheters, feeding tubes, drainage tubes, venous lines, and the like.

BRIEF SUMMARY OF THE INVENTION

The present invention has been developed in response to the current state of the art, and in particular, in response to these, and other, problems and needs that have not been fully or adequately resolved by currently available brushes. Briefly summarized, embodiments of the present invention provide an improved brush which facilitates, among other things, safe and effective cleaning of passageways defined by various medical devices without necessitating removal of the medical device from the patient or otherwise interrupting fluid communication between the patient and the medical device.

Embodiments of the present invention are well suited for use in the context of the cleaning of medical devices such as hemodialysis tubes, catheters, feeding tubes, drainage tubes, venous lines, and the like. However, it will be appreciated that embodiments of the present invention are suitable for use in any application or environment where it is desired to implement safe and effective in situ cleaning of a medical device defining one or more passageways in communication with, or otherwise connected to, a patient.

In one embodiment of the present invention, a brush is provided that includes an atraumatic tip comprising a core wire, preferably composed of a memory alloy such as NiTiNOL (Nickel Titanium Naval Ordnance Laboratory), and ground so that the core wire tapers from a relatively larger outside diameter at its proximal end to a relatively smaller outside diameter at its distal end. The proximal end of the core wire is preferably substantially flattened so as to overlap with a braided fill wire, discussed below. Disposed about the core wire is a coil, preferably comprising gold-plated tungsten. A suitable epoxy bonds the coil to the hollow core wire and to a distal connector sleeve, discussed below, within which the proximal end of the core wire is received. Finally, a bulb, preferably comprising medical grade epoxy, is disposed about the coil at the distal end of the core wire.

As suggested above, the atraumatic tip is joined to a fill wire, preferably comprising a plurality of braided wires, which includes a fill section comprising a plurality of bristles, or fill, preferably comprising nylon or the like. The braiding facilitates, among other things, a high degree of flexibility in the fill wire. The flattened end of the core wire is made to overlap with the distal end of the fill wire, which preferably comprises stainless steel, and the two are retained in place by way of the distal connector sleeve, preferably comprising stainless steel. Preferably, the distal connector sleeve is resistance welded to the proximal end of the core wire and to the distal end of the fill wire. The brush bristles, or fill, are incorporated during the braiding of the wire and the outside diameter of the fill section preferably increases from the distal end of the fill wire to the proximal end of the fill wire. The proximal end of the fill wire is joined to a shaft, preferably comprising NiTiNOL, by way of a proximal connector sleeve that is resistance welded to the fill wire and the shaft. Preferably, the proximal connector sleeve comprises stainless steel.

Finally, an inner sheath, preferably comprising a high temperature heat shrink paraffinic polymer, such as polytetrafluoroethylene (PTFE), is shrink wrapped around the portion of the brush extending from the proximal connector sleeve to the proximal end of the fill section of the fill wire. The inner sheath, in turn, is covered with an outer sheath that covers the entire shaft and extends up to the proximal end of the fill section. Preferably, the outer sheath, like the inner sheath, comprises PTFE (such as Teflon®).

In operation, the atraumatic tip of the brush is inserted into the passageway defined by a catheter, drainage tube, venous tube, or other medical device and pushed along the passageway until the fill is in position for cleaning. The flexibility imparted by the core wire, tungsten coil, fill wire, and NiTiNOL shaft permits the brush to readily negotiate the passageway defined by the medical device. Further, the tapered core wire and coil of the atraumatic tip are effective in facilitating cleaning of the passageway while also minimizing harm to the patient or to the medical device in which the brush is disposed.

Further, the downward taper of the fill, toward the distal end of the atraumatic tip, enables the distal end of the fill section to readily enter very small openings, such as may be encountered where there is substantial residue or a blockage of the passageway defined by the medical device. As the atraumatic tip is gradually worked into the blockage, the tapered outside diameter of the proximal end of the fill section is effective in enlarging the opening to the point that the blockage is ultimately removed. The bulb on the distal end of the atraumatic tip section further cooperates with the fill wire section to dislodge blockages and the like that are present in the passageway defined by the medical device.

Further, the inner sheath provides for a smooth transition from the braided fill wire to the distal connector sleeve and also serves to help prevent kinks in the fill wire as the fill section is worked through the blockage. Finally, the outer sheath further contributes to the ease with which the brush negotiates the passageway by substantially covering the fill wire and by implementing a transition between the fill wire and the shaft, thus providing the brush with a smooth, continuous outside coating of substantially constant diameter.

These and other advantages and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 7 is a side view illustrating details concerning an embodiment of a fill wire;

FIG. 8 is a side view illustrating various details concerning an embodiment of an atraumatic tip.

DETAILED DESCRIPTION OF EMBODIMENTS OF THE INVENTION

Reference will now be made to figures wherein like structures will be provided with like reference designations. It is to be understood that the drawings are diagrammatic and schematic representations of various embodiments of the claimed invention, and are not to be construed as limiting the present claimed invention in any way, nor are the drawings necessarily drawn to scale.

Figure 1:
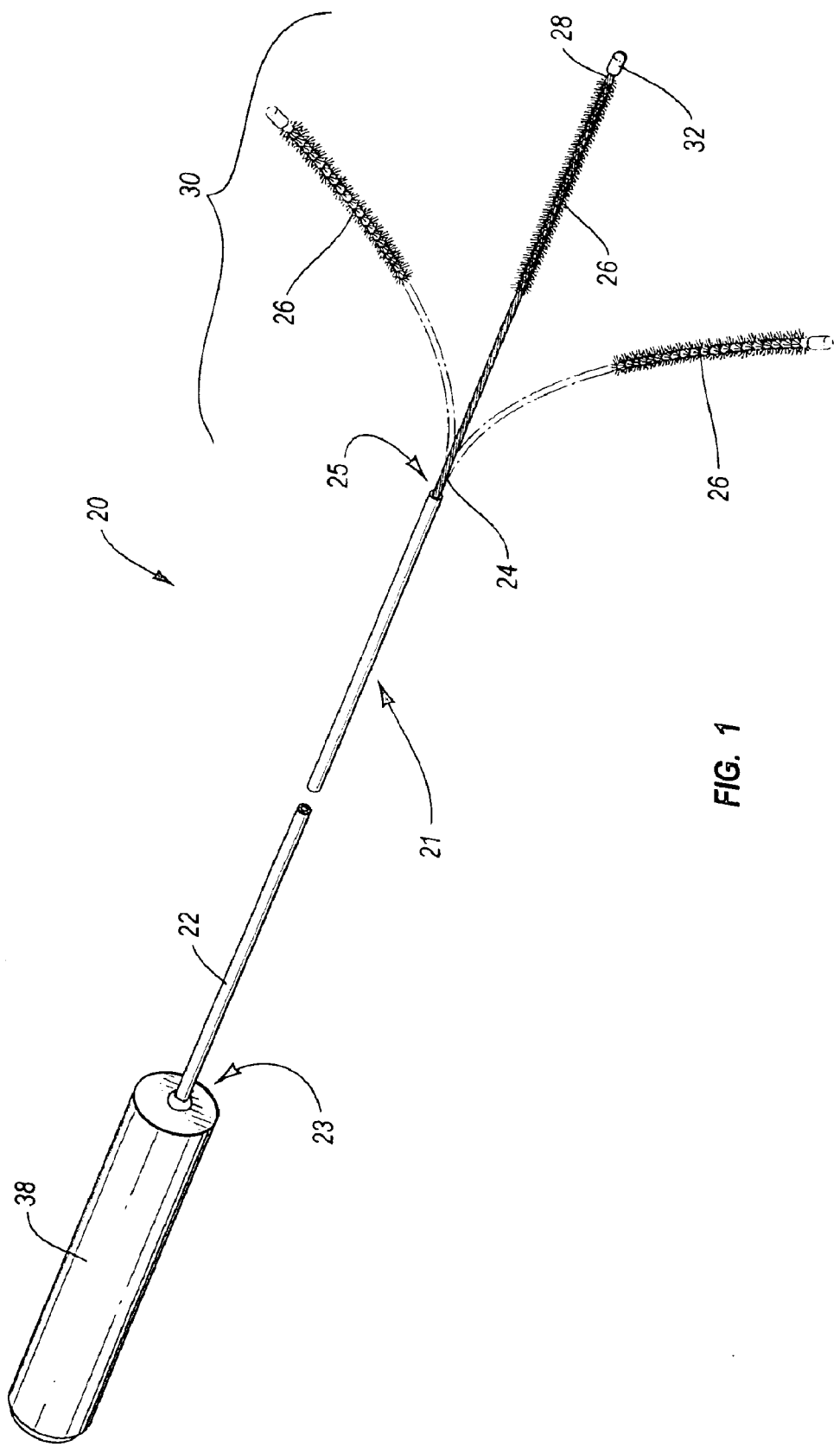
FIG. 1 is a partial perspective view of one embodiment of a brush for cleaning the interior passageway of a tubular member.

One embodiment of a brush for cleaning one or more passageways, or the like, defined by a medical device, is indicated generally at 20 in FIG. 1. Note that, as contemplated herein, such passageways include, but are not limited to, such passageways as are defined by hemodialysis tubes, catheters, feeding tubes, parenteral nutrition tubes, gastric catheters, drainage tubes, venous lines, and other medical devices. It will be appreciated however, that the foregoing applications and devices, and others disclosed herein, are presented solely by way of example and should not be construed or interpreted to limit the scope of the present invention in any way.

Generally, brush 20 includes an elongated shaft member 21 and bristles 26. Shaft member 21 has a proximal end 23 and a distal end 25. Distal end 25 of shaft member 21 is sufficiently flexible to follow the contour of the catheter, feeding tube, or venous line. Proximal end 23 of shaft member 21 has sufficient strength to transfer the forces caused by longitudinal movement of the brush to bristles 26. Brush 20 is sized and configured so as to be operated by a user while the medical device is fluidly connected to a patient.

In one embodiment, as illustrated in FIG. 1, shaft member 21 comprises elongated tube 22 and an elongated wire 24, which have sufficient strength to transfer the forces caused by longitudinal movement of brush 20 to bristles 26 with substantially no distortion or bending of tube 22 and wire 24. As depicted, tube 22 is cylindrical-shaped and has a proximal and distal end. Tube 22 could, however, have various other configurations and perform the function thereof. For example, tube 22 could be shaped as an oval, ellipse, octagon, square, or any combination thereof. Tube 22 comprises resilient, flexible materials, such as by way of example and not limitation, polymers and various kinds of plastic materials, metals or alloys thereof such as NiTiNOL, nickel alloys, titanium, or stainless steel. In one embodiment, tube 22 is made of a plastic material. Tube 22 has a longitudinal passageway (not shown) formed therethrough.

In one embodiment, wire 24 is longer than tube 22 and has a proximal end (not shown) and a distal end 28. As illustrated in FIG. 1, proximal end (not shown) of wire 24 is disposed in the longitudinal passageway of cylindrical tube 22. As a result, when the proximal end (not shown) of wire 24 is disposed in the passageway of tube 22, a portion 30 of distal end 28 of wire 24 extends beyond the distal end of tube 22. One embodiment of wire 24 is made up of individual threads that are manufactured using conventional methods so as to have a continuous twist along the length thereof. Wire 24 is comprised of a flexible, resilient material. Wire 24 may be comprised of polymers and various kinds of plastic materials, metals or alloys thereof such as NiTiNOL, nickel alloys, titanium, or stainless steel. In one embodiment, wire 24 comprises a stainless steel mandrel wire. It can be appreciated that wire 24 may simply be attached to the end of tube 22 rather than extending into the passageway of tube 22.

Wire 24 may have a constant diameter along the entire length thereof. As will be appreciated by those skilled in the art, the diameter of wire 24 is dependent on the size of the medical device which is to be cleaned. In an alternative embodiment, portion 30 of distal end 28 of wire 24 tapers in diameter to gradually towards distal end 28. In this embodiment, the diameter of wire 24 smoothly and continuously tapers from distal end 28 to proximal end.

Wire 24 and the passageway of tubing 22 are shown in FIG. 1 as having a substantially circular cross-section. It can be appreciated by those skilled in the art that wire 24 and the passageway of tubing 22 may have various other configurations and perform the function thereof. Generally, wire 24 and the passageway of tubing 22 are sized and configured to cooperate such that wire 24 can be disposed therein.

Portion 30 of distal end 28 of wire 24 which extends beyond tube 22 has sufficient flexibility that it can follow the contours of one or more passageways defined by a medical device. By way of example and not limitation, FIG. 1 depicts in phantom various positions that portion 30 of distal end 28 of wire 24 may assume.

As will be appreciate by one skilled in the art, shaft member 21 may have various other embodiment. Instead of comprising two pieces, shaft member 21, may alternatively comprise a one piece member which has a proximal end that has sufficient strength to transfer the forces imparted by the longitudinal movement of the brush to the bristles and a distal end that has sufficient flexibility to follow the contour of the catheter, feeding tube or venous line.

Brush 20 also includes a plurality of bristles 26 attached to portion 30 of distal end 28 of wire 24. Bristles 26 are fairly rigid and in one embodiment form a substantially circular cross-sectional bristle portion. The diameter formed by the remote end of bristles 26 may have various diameters configured to cooperate with various sizes of catheters or feeding tubes. Bristles 26 may comprise polymers, such as nylon, various kinds of plastic materials, metals or alloys thereof such as NiTiNOL, nickel alloys, titanium, or stainless steel. In one embodiment, bristles 26 are substantially composed of a nylon material.

It can be appreciated by one skilled in the art, that the remote end of bristles 26 could also form various configurations. For example, the profile formed by the remote end of bristles 26 could be tapered near distal end 28 of wire 24. In addition, bristles 26 may be in sections having differing cross-sectional profiles. Bristles 26 may form a conical shape or cylindrical shape. Further, bristles 26 could have differing orientations relative to shaft member 21.

Figure 2:
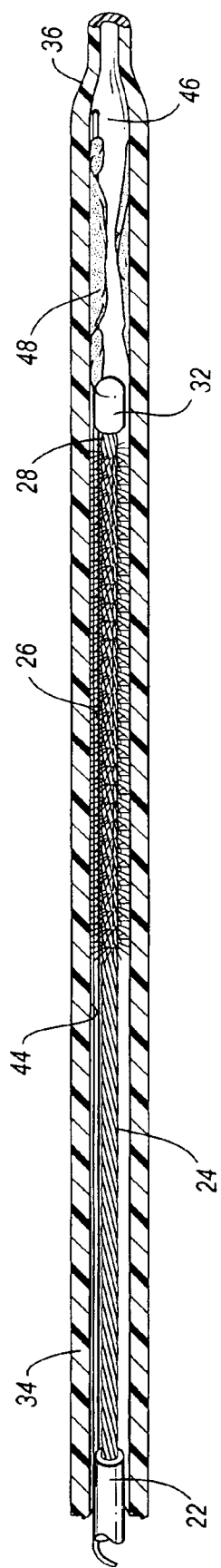
FIG. 2 is a partial cross-sectional view of the structure of FIG. 1 as the brush is inserted into one embodiment of a tubular member.

In the alternative, bristles 26 attached to portion 30 of distal end 28 of wire 24 could have various lengths rather than being substantially the same length as illustrated in FIG. 1. Bristles 26 are sized and configured regardless of the profile formed by the remote end thereof to contact the interior surface of the passageway of catheter or feeding tube 34 (FIG. 2). Bristles 26 are attached to wire 24 near distal end 28. Bristles 26 may be attached to wire 24 over various longitudinal lengths of wire 24 and perform the function thereof equally effectively.

Brush 20 also includes a distal tip 32 mounted to distal end 28 of wire 24. One embodiment of distal tip 32, as depicted in FIG. 1, is substantially cylindrical-shaped with the distal end thereof being semi-spherical. Distal tip 32 is comprised of polymers and various kinds of plastic materials, metals or alloys thereof such as NiTiNOL, nickel alloys, titanium, or stainless steel. One embodiment of distal tip 32 comprises a stainless steel material. Various other embodiments of distal tip 32 are equally effective in performing the function thereof. Distal tip 32 is substantially rounded to prevent any damage to either the interior passageway of the medical device or the tissue of the patient, and helps keep the distal end of brush 20 from passing beyond the end of the medical device.

For example, one embodiment of distal tip 32 is sized and configured such that when used, particularly with a catheter 34 such as the one shown in FIG. 2 that has a tapered end 36, helps to prevent distal end 28 of wire 24 from traveling beyond the end of a catheter, a feeding tube, or venous line and harming the tissue of the patient. Tapered end 36 of catheter 34 is disposed within the patient (not shown). Brush 20 cannot travel beyond tapered end 36 of this embodiment of catheter 34. It can be appreciated by those skilled in the art that the end of all catheters 34 may not be tapered. Brush 20, however, works equally effectively in those catheters, feeding tubes, or venous lines that are not tapered. Brush 20 comes in various lengths depending on the size and type of catheter, feeding tube, or venous line that is being utilized. Wire 24 of brush 20 has is available in various lengths depending on the type of catheter, feeding tube, or venous line that brush 20 is to be used. As a result, brush 20 will be of such a length that the probability of brush 20 extending beyond the end of catheter or feeding tube into patient is remote.

Referring back to FIG. 1, brush 20 also includes a handle 38 that is attached to proximal end of shaft member 21. Specifically, handle 38 is connected to proximal end (not shown) of wire 24 and proximal end of tube 22. Handle 38 is sized and configured so as to be comfortable in the hand of the medical personnel who will use brush 20 to clean the medical device while the medical device is fluidly connected to the patient. Handle 38 may comprise a plastic or other polymer material. Handle 38 is sized and configured so as to be able to cooperate with an adapter (not shown) that is attached to one end of a fluid line so that a cleaning solution can be supplied to interior passageway of catheter or feeding tube to enhance the cleaning implemented by way of brush 20. The adaptor is configured to receive brush therethrough and to be attached the catheter or feeding tube. The adaptor may include a conventional male or female Luer lock that is configured to cooperate with the Luer lock that is typically on the exit end of the catheter or feeding tube.

Figure 3:
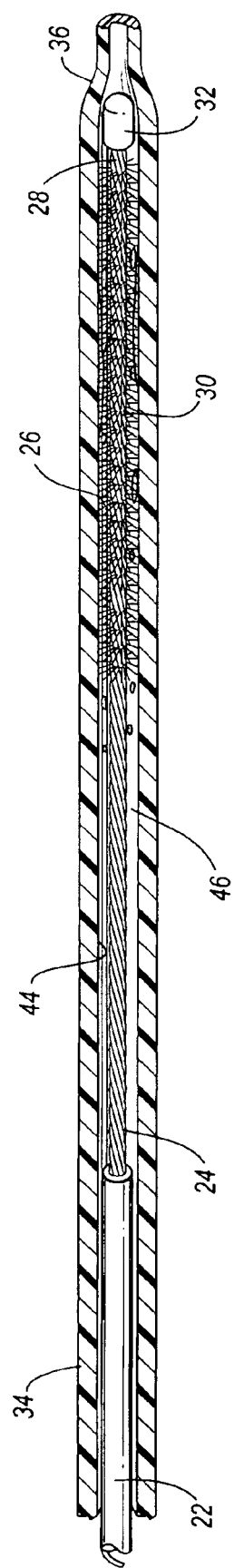
FIG. 3 is a partial cross-sectional view of the structure of FIG. 1 in use.

In use, as depicted in FIGS. 2 and 3, brush 20 is inserted into the catheter, feeding tube, or venous line 34. Catheter, feeding tube, or venous line has an optional retention string (not shown). Bristles 26 are sized and configured depending on the size of catheter, feeding tube, or venous line to contact the interior surface 44 of the interior passageway 46 thereof. As previously mentioned, wire 24 is a resilient, flexible member capable of following the contour and curves of catheter or feeding tube 34. While tube 22 is also a resilient, flexible member, the addition of tube 22 around a substantial portion of wire 24 provides additional strength and rigidity sufficient to transfer the forces being applied by medical personnel cleaning catheter, feeding tube, or venous line. The user applies force through the handle to effectively create a scrubbing motion to dislodge and remove any build-ups formed by particles, residues, and the like, such as build-up 48, formed on interior surface 44 of interior passageway 46 of catheter or feeding tube 34 or the optional residual string that resides in the catheter, feeding tube, or venous line.

As FIG. 3 illustrates, the scrubbing motion of brush 20 causes bristles 26 to dislodge the particles and eventually break down any build-ups that have occurred on the wall 44 of the interior passageway 46 of catheter, feeding tube, or venous line or the optional string. The unique design of brush 20 allows catheter, feeding tube, or venous line to be cleaned while it is still in place in the patient and fluidly connected to the patient rather than having to be removed. Once the passageway of the medical device has been cleaned and the particles dislodged, bristles 26 help remove the loose particles from passageway 46 of catheter, feeding tube, or venous line. In addition and as previously mentioned, brush 20 is adapted to be utilized with an adapter so as to place the catheter, feeding tube, or venous line in fluid communication with a fluid line that flushes the catheter, feeding tube, or venous line with a cleaning solution either during use of the brush or immediately following to clear out the loose particles. The cleaning solution typically is saline but may alternatively comprise other suitable cleaning and/or sterilization agents.

It can be appreciated by one skilled in the art that shaft member 21 may have various other embodiments. For example, instead of wire 24 extending all the way through and being disposed in the passageway of tubing 22, wire 24 may be attached to the distal end of tubing 22. In this embodiment, wire 24 would not extend substantially into the passageway of tubing 22. In this embodiment where wire 24 is attached to the proximal of tubing 22, tubing 22 may be a solid member or, in the alternative, tubing 22 may be hollow with passageway formed therethrough.

Figure 4:
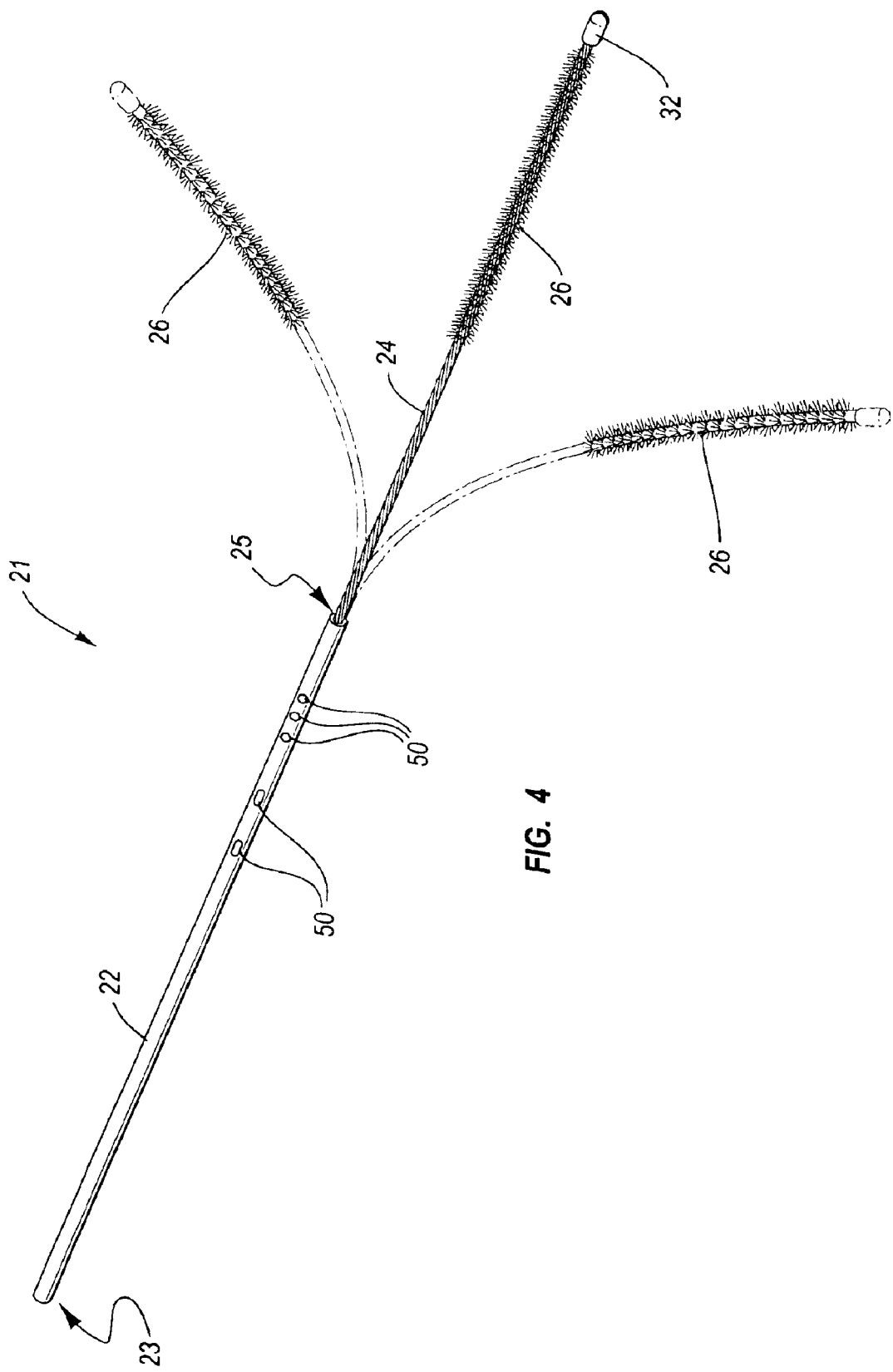
FIG. 4 is a partial view of an alternative embodiment of a brush.

In an alternative embodiment, depicted in FIG. 4, shaft member 21 of brush 20 is configured so that proximal end of wire 24 is attached to distal end 25 of tubing 22. In this embodiment, tubing 22 would define a passageway (not shown) formed therethrough. The portion of tubing 22 proximate to distal end of the passageway has a plurality of holes, slits, or other shapes of openings 50 formed therein. In general, openings 50 allow brush 20 to be used to clean the passageway of the catheter, feeding tube, venous line, or other medical device while simultaneously infusing the passageway of the medical device with fluid. Therefore, this embodiment of brush 20 has the advantage, among others, that it allows scrubbing at the same time as the particles which are broken up are flushed away.

Figure 5:
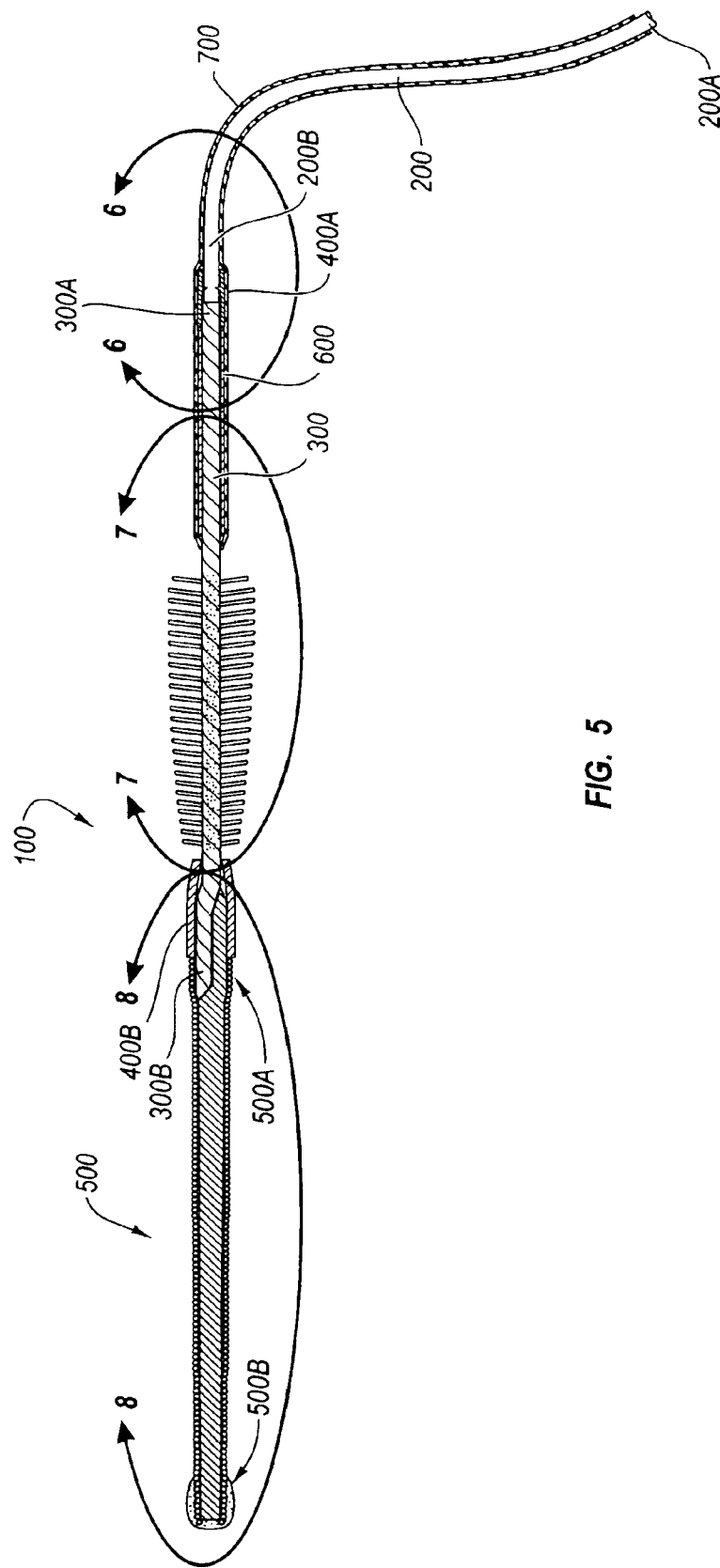
FIG. 5 is a cutaway view illustrating various details of an embodiment of the present invention.

Directing attention now to FIGS. 5 through 9, details are provided regarding an alternative embodiment of a brush. With particular reference to FIG. 5, an embodiment of a brush is indicated at 100. In general, brush 100 includes a shaft 200 having a proximal end 200A and distal end 200B. Abutting shaft 200 is a fill wire 300 having a proximal end 300A and distal end 300B. Fill wire 300 and shaft 200 are joined together by way of proximal connector sleeve 400A which is configured and arranged to receive a portion of distal end 200B of shaft 200 and a portion of proximal end 300A of fill wire 300. Brush 100 additionally includes atraumatic tip 500, which is joined to fill wire 300 by distal connector sleeve 400B. More specifically, atraumatic tip 500 includes a proximal end 500A and distal end 500B. Distal connector sleeve 400B receives a portion of proximal end 500A of atraumatic tip 500, as well as a portion of distal end 300B of fill wire 300. Further, an inner sheath 600 covers a portion of fill wire 300 and terminates, preferably, proximate to proximal connector sleeve 400B. Finally, shaft 200 and inner sheath 600 are covered by outer sheath 700.

Figure 6:
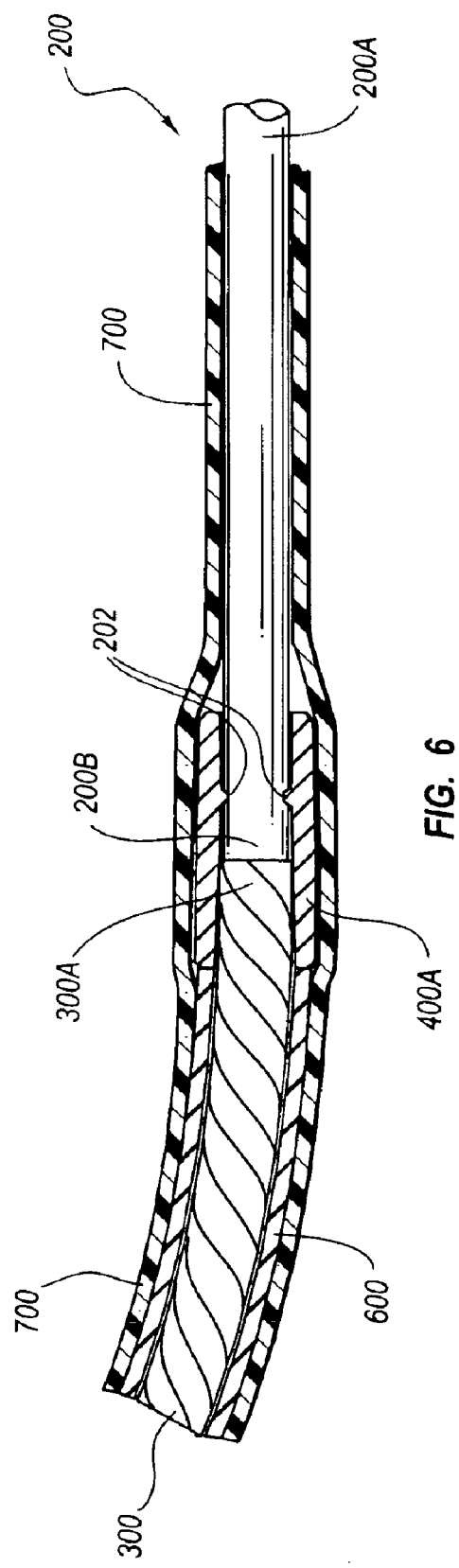
FIG. 6 is a side view illustrating various details of an embodiment of a shaft and fill section.

Directing attention now to FIG. 6, details are provided regarding an embodiment of shaft 200. Generally, shaft 200 includes a proximal end 200A and a distal end 200B, and is preferably composed of a memory alloy such as NiTiNOL or the like. It will be appreciated however, that with respect to shaft 200 (and core wire 502 discussed below), various other materials, or combinations thereof, which exhibit "shape memory" or "superelastic" properties are likewise suitable and are, accordingly, contemplated as being within the scope of the present invention. Distal end 200B further defines a notch 202 or the like, disposed circumferentially around shaft 200.

Preferably, distal end 200B of shaft 200 is arranged to abut proximal end 300A of fill wire 300 (FIG. 7). Shaft 200, and fill wire 300, are retained in place with respect to each other by way of proximal connector sleeve 400A which is preferably composed of medical grade stainless steel or the like. In particular, a portion of distal end 200B of shaft 200, and a portion of fill wire 300, are received and retained in proximal connector sleeve 400A. Preferably, proximal connector sleeve 400A is slightly crimped onto shaft 200 so that a portion of proximal connector sleeve 400A is forced into notch 202, thereby forming a mechanical connection between proximal connector sleeve 400A and shaft 200. Finally, proximal connector sleeve 400A is joined, preferably by a process such as crimping or the like, to shaft 200 and to fill wire 300. Alternatively, proximal connector sleeve 400A may be joined to shaft 200 and/or to fill wire 300 by processes such as resistance welding, or the like.

It will be appreciated that the flexibility and strength of shaft 200 provide for various desirable characteristics with respect to the operation of brush 100. By way of example, the flexibility of shaft 200 permits brush 100 to readily negotiate the passageways defined by medical devices such as hemodialysis tubes, feeding tubes, catheters, and the like. Further, the NiTiNOL, with which shaft 200 is preferably constructed, is well suited to withstand the cleaning forces typically applied to brush 100, and accordingly contributes to the overall durability and service life of brush 100.

Directing attention now to FIG. 7, various details are provided regarding an embodiment of fill wire 300. In general, fill, wire 300 has a proximal end 300A, a portion of which is received in proximal connector sleeve 400A as discussed above, and distal end 300B, and also includes a fill section 302 having a plurality of bristles, or fill, 302A, joined to, or otherwise connected with, fill wire 300. In general, "fill section" refers to that portion of fill wire 300 wherein fill 302 is located. Fill wire 300 comprises a plurality of braided wires, preferably comprising medical grade stainless steel or the like. However, it will be appreciated that various other materials, braided or otherwise, having the properties of stainless steel may be substituted.

In one embodiment of the invention, fill 302A is incorporated in fill wire 300 by being twisted into the braided wires during manufacturing. Optionally, epoxy or other suitable adhesive may additionally be applied to fill 302A to further facilitate the retention of fill 302A in fill wire 300. Finally, it will be appreciated that various other structures and/or methods may be employed to securely attach fill 302A to fill wire 300. By way of example, in one alternative embodiment, fill section 302 comprises a discrete structure that is disposed about fill wire 300 and joined thereto by resistance welding or other similar process.

As indicated in FIG. 7 (and FIG. 5), fill 302A preferably terminates somewhat short of distal end 300B of fill wire 300 so as to permit attachment of fill wire 300 to atraumatic tip 500 (FIGS. 5 and 8). Preferably, fill 302A comprises medical grade nylon or the like. However, it will be appreciated that various other materials may be employed consistent with contemplated applications of embodiments of the present invention.

In one embodiment of the present invention, an outside diameter ("OD") defined by fill 302A of fill section 302 gradually decreases, or tapers, toward distal end 300B of fill wire 300. Such a configuration permits, among other things, ready passage of brush 100 through a passageway defined by a medical device. The tapered configuration also allows fill 302A to be gradually worked into a blockage or other material.

It will be appreciated that embodiments of brush 100 may be employed in a variety of applications and, accordingly, variables including, but not limited to, the geometry defined by fill 302A, as well as the size, and/or orientation of fill 302A may be varied either alone or in various combinations as required to suit a particular application and/or to facilitate achievement of one or more desired results. By way of example, an untapered fill 302A geometry may be desirable in some applications. As another example, shorter, or longer, fill sections 302 may be employed to suit a particular desired application.

Directing attention now to FIG. 8, additional details are provided concerning atraumatic tip 500. In particular, atraumatic tip 500 includes a core wire 502, preferably comprising a memory alloy such as NiTiNOL or the like. It will be appreciated however, that various other materials, or combinations thereof, that exhibit "shape memory" or "super-elastic" properties are likewise suitable and are, accordingly, contemplated as being within the scope of the present invention. As discussed elsewhere herein, such properties permit brush 100 to readily negotiate passageways within which brush 100 is deployed.

With respect to its geometry, core wire 502 preferably comprises a "centerless ground" wire, and tapers from a relatively larger OD at proximal end 502A to a relatively smaller OD at distal end 502B. Operationally, the taper facilitates ready penetration and breakup of blockages and the like, such as are typically encountered in many medical devices, while the relatively larger OD portion of the taper lends sufficient strength to core wire 502 as to facilitate ready and effective transmission of a cleaning force to the blockage.

It will be appreciated that variables including, but not limited to, the length of core wire 502, the degree and length of the taper, the diameter of core wire 502, and the cross-sectional shape of core wire 502, may be varied either alone or in various combinations as required to suit a particular application and/or to facilitate achievement of one or more desired results. It will further be appreciated that in some embodiments of the invention, no taper is provided.

With continuing reference to various geometric features of core wire 502, at least a portion of proximal end 502A of core wire 502 is preferably flattened, or otherwise shaped, so as to readily fit together with distal end 300B of fill wire 300 within distal connector sleeve 400B, as suggested in FIG. 5. However, it will be appreciated that various other geometries of proximal end 502A of core wire 502 and/or distal end 300B of fill wire 300 may alternatively be employed to facilitate the joining of atraumatic tip 500 and fill wire 300. Preferably, distal connector sleeve 400B is joined to core wire 502 and fill wire 300 by resistance welding or related process.

In addition to core wire 502, atraumatic tip 500 also includes coil 504 disposed about core wire 502. Preferably, coil 504 comprises a radio-opaque material such as gold-plated tungsten, or the like, which can be readily detected by a fluoroscopy process. However, any other material or combination of materials, platinum for example, having the functionality of gold-plated tungsten, as disclosed herein, are contemplated as being within of the present invention. Finally, a suitable adhesive, preferably a medical grade epoxy or the like, bonds coil 504 to core wire 502 and to distal connector sleeve 400B. Finally, it will be appreciated that variables including, but not limited to, the size, geometry, number, disposition, and/or materials, of the individual coils that comprise coil 504 may be varied either alone or in various combinations as required to suit a particular application.

With continuing reference to FIG. 8, atraumatic tip 500 additionally includes a bulb 506 disposed about that portion of coil 504 proximate distal end 502B of core wire 502. Preferably, bulb 506 comprises epoxy, weld material, or the like. In general, bulb 506 provides a rounded surface that serves to cover any sharp edges present in coil 504 or distal end 502B of core wire 502. In this way, bulb 506 lends an "atraumatic" characteristic to brush 100. That is, bulb 506 helps foreclose damage or harm to the medical device or to the patient in which the medical device (FIG. 9) is disposed, that could otherwise result from sharp edges and the like present either on coil 504 and/or distal end 502B of core wire 502. In addition to neutralizing sharp or rough edges on coil 504 and/or distal end 502B of core wire 502, bulb 506 also cooperates with the tapered construction of core wire 502 to effectively penetrate and clear blockages (FIG. 9), and the like, within a passageway defined by a medical device, without causing injury or harm either to the medical device or to the patient in which the medical device is disposed.

Finally, it will be appreciated that a variety of other structures, and/or combinations thereof, may be profitably employed to perform the collective functions, enumerated herein, of fill wire 300 and atraumatic tip 500. Accordingly, fill wire 300 and atraumatic tip 500 collectively comprise but one example of a means for transmitting a cleaning force. In one alternative embodiment, for example, a plurality of fill sections 302 are provided in the context of fill wire 300. It should accordingly be understood that the embodiments of fill wire 300 and atraumatic tip 500, as well as the arrangements of fill wire 300 and atraumatic tip 500, are presented herein solely by way of example and should not be construed as limiting the scope of the present invention in any way.

In view of the foregoing, it will be appreciated that one desirable feature of embodiments of the present invention is that the atraumatic characteristics of brush 100 permit brush 100 to be used to safely and effectively clean a passageway defined by a medical device even while the medical device is attached to, or otherwise in communication with, a patient. An advantage of such functionality is that the catheter, feeding tube, or other medical device that is in communication with the patient need not be removed in order to be cleaned and may be used for a relatively longer period of time than would otherwise be the case. As a result, the likelihood of infection, or other undesirable consequences, that typically attend the change out of catheters and other medical devices is substantially reduced. Further, the pain experienced by the patient due to the change out of the medical device is substantially reduced as well because the number of change outs is minimized. Finally, because the same medical device can be cleaned repeatedly, the need for multiple additional medical devices is minimized and a cost savings accordingly realized.

Directing renewed attention now to FIGS. 5 through 7, details are provided regarding additional features of embodiments of the present invention. In particular, embodiments of the present invention include an inner sheath 600 that extends, preferably, from a point proximate fill section 302 up to proximal connector sleeve 400A and serves to provide, among other things, a relatively smooth and continuous transition between the OD of fill wire 300 and the OD of proximal connector sleeve 400A.

The smooth transition thus provided permits brush 100 to easily pass through and negotiate the small passageways typically encountered in medical devices. Additionally, inner sheath 600 serves to protect fill wire 300 which, due to its braided construction, would otherwise be susceptible to kinking or other deformation or damage. Preferably, inner sheath 600 comprises a medical grade PTFE material, such as Teflon® or the like, applied through the use of a high temperature heat shrink process. However, it will be appreciated that various other materials, nylon for example, may be substituted.

In addition to inner sheath 600, embodiments of brush 100 further comprise an outer sheath 700 disposed and arranged so as to substantially cover shaft 200 as well as inner sheath 600. Preferably, sheath 700 extends somewhat beyond the terminal point of inner sheath 600 proximate to fill 302A, as indicated in FIG. 7. As in the case of inner sheath 600, sheath 700 comprises a low-friction material, preferably a medical grade PTFE material such as Teflon® or the like, and is applied through a high temperature heat shrink process. Sheath 700 serves to improve the overall durability of brush 100 and also to give the outer surface of brush 100 a substantially constant diameter, and continuity, so as to permit brush 100 to readily negotiate passageways of the medical device with which brush 100 is employed. Further, the low friction properties of sheath 700 are also helpful in allowing brush 100 to negotiate complex and/or obstructed passageways.

Finally, embodiments of the present invention include a handle, or similar structure (not shown) attached or secured to proximal end 200A of shaft 200. Such a handle permits an operator to impart a desired action and cleaning force to brush 100.

Figure 9:
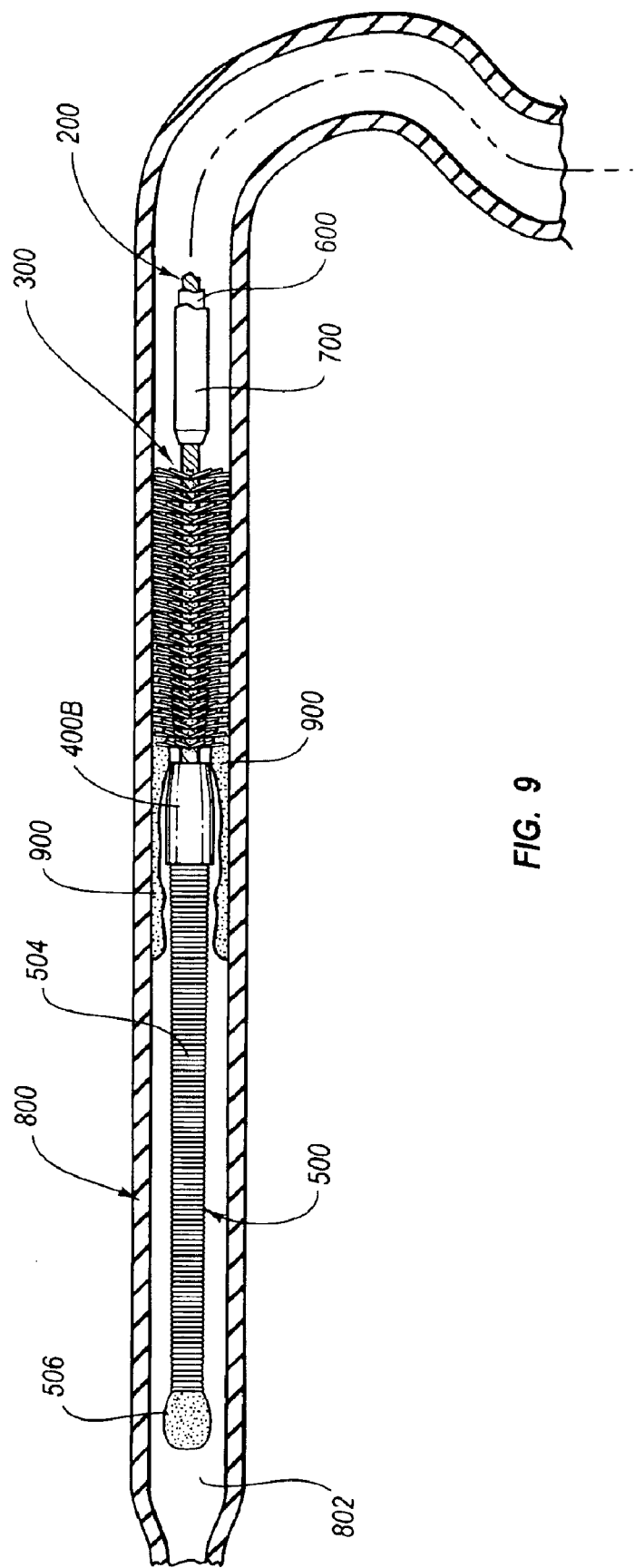
FIG. 9 illustrates one exemplary application for an embodiment of the present invention.

Directing attention now to FIG. 9, details are provided regarding one exemplary application of an embodiment of the present invention. In general, it will be appreciated that embodiments of the present invention are suitable for use in any application or environment where it is desired to implement safe and effective in situ cleaning of a medical device 800 defining one or more passageways 802 in communication with, or otherwise connected to, a patient. Examples of medical devices 800 which provide suitable operating environments for the present invention include, but are not limited to, hemodialysis tubes, catheters, feeding tubes, drainage tubes, venous lines, and the like.

Embodiments of the present invention are particularly well suited for situations where it is desired to remove blockage 900 while maintaining communication between passageway 802 and the patient. It will be appreciated that the illustrated blockage 900 is exemplary only and that residue, buildup, blockages, and/or other undesirable materials present in passageway 802 may take various forms and/or have various characteristics.

In operation, brush 100 is inserted into passageway 802 and advanced forward towards obstruction 900 until atraumatic tip 500 contacts obstruction 900. As discussed elsewhere herein, the flexibility imparted to brush 100 by shaft 200, fill wire 300, and atraumatic tip 500, permits brush 100 to readily negotiate passageway 802 without becoming kinked, jammed, or otherwise stuck in passageway 802. Thus, embodiments of the present invention are able to readily negotiate even the most complex and circuitous passageways 802. Further, the taper of core wire 502 cooperates with the geometry of bulb 506 to ensure that while brush 100 is rigid enough to advance easily along passageway 802 and break up blockage 900, brush 100 is likewise sufficiently flexible and atraumatic to generally foreclose the possibility of harm either to the medical device in which brush 100 is disposed, or to the patient.

At such time as atraumatic tip 500 contacts blockage 900, brush 100 is then moved about as required to ensure the breakup and ultimate removal of blockage 900. Generally, bulb 506 serves to initiate breakup of blockage 900 and cooperates with fill 302A to ultimately completely break up blockage 900 so that blockage 900 no longer impedes flow though passageway 802. It will be appreciated that the necessary cleaning force may be transmitted to blockage 900 by various movements of brush 100. By way of example, brush 100 may be moved back and forth within passageway 802 and/or may be rotated within passageway 802. Finally, embodiments of brush 100 may be employed in conjunction with various cleaning solutions and/or chemicals including, but not limited to, saline solutions.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A brush for use in cleaning a passageway defined by a medical device, said brush comprising:
   (a) a shaft with a flexible tube portion and a wire portion, said tube portion having a proximal end and a distal end, wherein a portion of said distal end of said tube portion has a plurality of openings formed therein, wherein said plurality of openings are in fluid communication with said proximal end of said tube portion;
   (b) said wire portion having a proximal end and a distal end, said proximal end of said wire portion being attached to said distal end of said tube portion near said plurality of openings; and
   (c) a fill, said fill being attached to distal end of said wire portion.

2. The brush as recited in claim 1, wherein a tip is attached to said distal end of said wire portion, said tip being substantially cylindrically shaped and including a distal end, said distal end of said tip being semi-spherical.

3. The brush as recited in claim 1, wherein a handle is attached to said proximal end of said tube portion.

4. The brush as recited in claim 3, wherein said handle is sized and configured to be able to cooperate with an adapter, said adapter comprising a male or female Luer lock configured to cooperate with a complimentary Luer lock on the exit of a passageway of a medical device.

5. The brush as recited in claim 1, wherein said fill comprises bristles.

6. A brush for cleaning a passageway defined by a medical device, comprising:
   (a) a shaft portion, said shaft portion including a proximal end and a distal end;
   (b) a fill wire, said fill wire having a proximal end and a distal end, said fill wire including a fill section;
   (c) a first connector sleeve, said first connector sleeve having a proximal end and a distal end, with said proximal end of said first connector sleeve configured to receive said distal end of said shaft portion, and said distal end of said first connector sleeve configured to receive said proximal end of said fill wire;
   (d) an atraumatic tip, said atraumatic tip having a proximal end and a distal end;
   (e) a second connector sleeve, said second connector sleeve having a proximal end and a distal end, said proximal end of said second connector sleeve configured to receive said distal end of said fill wire, and said distal end of said second connector sleeve configured to receive said proximal end of said atraumatic tip;
   (f) an inner sheath, said inner sheath covering a portion of said fill wire from at least a point at which said proximal end of said fill wire is received into said distal end of said first connector sleeve; and
   (g) an outer sheath, said outer sheath extending from said proximal end of said shaft portion to a point near said fill section, and covering said inner sheath.

7. The brush as recited in claim 6, wherein said fill section is tapered.

8. The brush as recited in claim 6, wherein said fill section comprises bristles.

9. The brush as recited in claim 6, wherein at least said shaft portion is composed of NiTiNOL.

10. The brush as recited in claim 6, wherein said first connector sleeve and said second connector sleeve are substantially composed of stainless steel.

11. The brush as recited in claim 6, wherein at least said inner sheath is substantially composed of polytetrafluoroethylene.

12. The brush as recited in claim 6, wherein at least said outer sheath is substantially composed of polytetrafluoroethylene.

13. The brush as recited in claim 6, wherein said distal end of said shaft portion includes a notch disposed circumferentially therearound such that when said distal end of said shaft portion is inserted in said proximal end of said first connector sleeve a mechanical connection is formed.

14. The brush as recited in claim 6, wherein said atraumatic tip comprises a core wire, said core wire having a proximal end and a distal end, said proximal end of said core wire and said distal end of said core wire corresponding in position to said proximal end of said atraumatic tip and said distal end of said atraumatic tip.

15. The brush as recited in claim 14, wherein said core wire is tapered.

16. The brush as recited in claim 14, wherein at least said core wire is substantially composed of a memory alloy.

17. The brush as recited in claim 14, wherein at least said core wire is substantially composed of NiTiNOL.

18. The brush as recited in claim 14, wherein a coil is disposed about said core wire.

19. A brush for cleaning a passageway of a medical device, said brush comprising:
   (a) a shaft portion, said shaft portion having a tube portion and a wire portion, said tube portion having a proximal end and a distal end, and said wire portion having a proximal end and a distal end;
   (b) a fill, said fill being attached to said distal end of said wire portion; and
   (c) an atraumatic tip, said atraumatic tip having a proximal end and a distal end, said proximal end of said atraumatic tip being attached to said distal end of said wire portion near said fill, said atraumatic tip including a core wire, said core wire of said atraumatic tip having a proximal end and a distal end, said proximal end of said core wire and said distal end of said core wire corresponding to said proximal end of said atraumatic tip and said distal end of said atraumatic tip, wherein said atraumatic tip has sufficient flexibility to lead said fill through the passageway of the medical device.

20. The brush as recited in claim 19, wherein said atraumatic tip further comprises a coil, said coil being disposed about said core wire.

21. The brush as recited in claim 20, wherein a bulb disposed about a portion of said coil near said distal end of said core wire.

22. The brush as recited in claim 21, wherein said bulb is substantially composed of epoxy.

23. The brush as recited in claim 19, wherein a handle is attached to said proximal end of said tube portion.

24. The brush as recited in claim 19, wherein at least a portion of said shaft portion is composed of NiTiNOL.

25. A brush for use in cleaning a passageway defined by a medical device, said brush comprising:
   (a) a shaft having distal and proximal ends;
   (b) a fill, said fill being connected to said distal end of said shaft;
   (c) an atraumatic tip having distal and proximal ends, said proximal end of said atraumatic tip being connected to said distal end of said shaft near said fill; and
   (d) a distal connector sleeve, wherein at least a portion of said proximal end of said atraumatic tip and at least a portion of said distal end of said shaft is received and retained in said distal connector sleeve, such that said proximal end of said atraumatic tip is connected to said distal end of said shaft.

26. The brush is recited in claim 25, wherein a bulb is connected to said distal end of said atraumatic tip.

27. The brush is recited in claim 26, wherein said bulb is substantially composed of epoxy.

28. A brush for cleaning a passageway of a medical device, said brush comprising:
   (a) a shaft portion, said shalt portion having a tube portion and a wire portion, said tube portion having a proximal end and a distal end, and said wire portion having a proximal end and a distal end;
   (b) a fill, said fill being attached to said distal end of said wire portion; and
   (c) an atraumatic tip, said atraumatic tip having a proximal end and a distal end, said proximal end of said atraumatic tip being attached to said distal end of said wire portion near said fill, said atraumatic tip including a core wire, wherein said atraumatic tip has sufficient flexibility to lead said fill through the passageway of the medical device.

* * * * *